US009282913B2

United States Patent
Jeon et al.

(10) Patent No.: US 9,282,913 B2
(45) Date of Patent: Mar. 15, 2016

(54) APPARATUS AND METHOD FOR SELF-EXAMINING ABNORMALITY OF BREAST TISSUE

(71) Applicant: ELECTRONICS AND TELECOMMUNICATIONS RESEARCH INSTITUTE, Daejeon (KR)

(72) Inventors: Soon Ik Jeon, Daejeon (KR); Hyung Do Choi, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 244 days.

(21) Appl. No.: 13/937,359

(22) Filed: Jul. 9, 2013

(65) Prior Publication Data

US 2014/0316260 A1    Oct. 23, 2014

(30) Foreign Application Priority Data

Apr. 22, 2013    (KR) .................. 10-2013-0044110

(51) Int. Cl.
*A61B 5/05*    (2006.01)
*A61B 5/00*    (2006.01)

(52) U.S. Cl.
CPC .............. *A61B 5/0507* (2013.01); *A61B 5/4312* (2013.01)

(58) Field of Classification Search
CPC .. A61B 5/0091; A61B 5/0095; A61B 5/4312; G01N 21/1702; G01N 21/255; G01N 29/0609; G01N 29/0672
See application file for complete search history.

(56) References Cited

U.S. PATENT DOCUMENTS

| 5,713,356 | A | * | 2/1998 | Kruger ......................... 600/407 |
| 6,212,421 | B1 | * | 4/2001 | Vo-Dinh et al. ............... 600/407 |
| 6,979,292 | B2 | | 12/2005 | Kanayama et al. |
| 2003/0069491 | A1 | * | 4/2003 | Kruger ......................... 600/407 |
| 2006/0058606 | A1 | * | 3/2006 | Davis et al. ................... 600/407 |

FOREIGN PATENT DOCUMENTS

| JP | 09-117417 A | 5/1997 |
| KR | 1020040007504 A | 1/2004 |
| KR | 10-0805463 B1 | 2/2008 |
| KR | 1020100002852 A | 1/2010 |
| WO | 02/086792 A2 | 10/2002 |

OTHER PUBLICATIONS

Tonny Rubaek, et al; "Nonlinear Microwave Imaging for Breast-Cancer Screening Using Gauss-Newton's Method and the CGLS Inversion Algorithm", IEEE Transactions on Antennas and Propagation, vol. 55, No. 8, Aug. 2007; pp. 2320-2331.

* cited by examiner

*Primary Examiner* — Joel Lamprecht
(74) *Attorney, Agent, or Firm* — Ladas & Parry LLP (57) ABSTRACT

An apparatus for self-examining whether a breast tissue is abnormal includes an examination checker configured to transmit a microwave to one side of an examinee's breast, receive the microwave that has passed through the breast and calculate a value in the microwave reception of the received microwave. Further, the apparatus includes a self-examination device configured to analyze the value in the microwave reception received from the examination checker and examines whether the breast is abnormal.

13 Claims, 5 Drawing Sheets

APPARATUS AND METHOD FOR SELF-EXAMINING ABNORMALITY OF BREAST TISSUE

CROSS-REFERENCE TO RELATED APPLICATION(S)

The present invention claims priority of Korean Patent Application No. 10-2013-0044110, filed on Apr. 22, 2013, which is incorporated herein by reference.

FIELD OF THE INVENTION

The present invention relates to a self-examination apparatus for an examinee, and more particularly, to an apparatus and method for self-examining whether a breast tissue is abnormal, capable of conveniently diagnosing whether an examinee's specific body part to be checked such as a breast, is abnormal without expensive medical equipments such as ultrasonic equipment, radiation equipment and magnetic field equipment, by embodying an examination checker that transmits a microwave to the examinee's body part, receives a response microwave, and generates microwave information, and a self-examination device installed in a mobile terminal such as a smart phone in a form of an application that analyzes microwave information provided by the examination checker and determines whether an examinee's breast tissue is abnormal.

BACKGROUND OF THE INVENTION

Recently, an active research has been made to develop a telemedicine system with which an examinee can take a treatment without having to go to the hospital.

An example of such a telemedicine system is as follows. When a pregnant woman wishes to take a telemedicine course, generally, she visits a medical institution to take a checkup list that can be self-measured at home and checkup kits needed for the checkup. She can transmit data self-measured at home to a telemedicine server of the medical institution via the Internet on-line. Then, a medical doctor at the medical institution remotely diagnoses this case using the data and informs the pregnant woman of the results.

Figure 1:
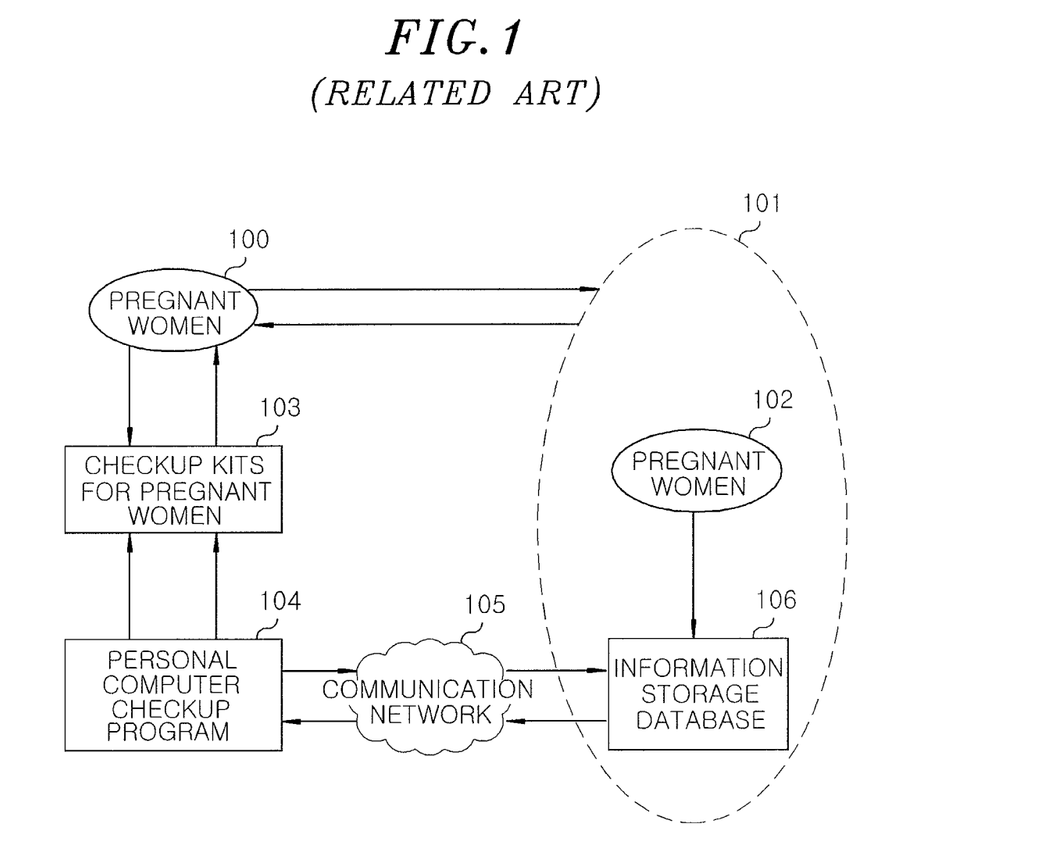
FIG. 1 is a conceptual view illustrating a telemedicine system for a pregnant woman in the related art.

FIG. 1 is a conceptual diagram illustrating a telemedicine system for a pregnant woman in the related art. Hereinafter, operations of the conventional telemedicine system will be described with reference to FIG. 1.

Referring to FIG. 1, first, a pregnant woman 100 visits a medical institution 101, and the medical institution 101 assigns a medical attendant 102 in charge of an On-line telemedicine and provides the pregnant woman 100 with checkup kits 103. The pregnant woman 100 then installs a telemedicine program of the checkup kits for pregnant women in a personal computer 104 at home and performs a self-measurement. Subsequently, the pregnant woman 100 inputs a result measured into the telemedicine program and transmits it to a medical server/client information storage database 106 for the telemedicine in the medical institution by way of a communication network 105.

Thereafter, the medical attendant 102 performs a diagnosis using the self-measured result of the pregnant woman by accessing to the information storage database 106 for telemedicine, stores a medical attendant's opinion and diagnosis in the medical server/client information storage database 106 for telemedicine, and informs the pregnant woman of diagnosis completion matters by way of the communication network 105. Then, the pregnant woman 100 confirms the information and checks diagnosis results by accessing to the medical server/client information storage database 106 in the medical institution 101.

As reviewed above, in the conventional telemedicine system for pregnant women, the pregnant woman transmits a self-measured examination results to a medical institution and determines whether there is an abnormality using an analysis performed in the medical institution. So, there is no suggestion for means to determine whether there is an abnormality using the self-measured results in a self-examination device.

Accordingly, since the pregnant woman has to transmit the self-measured results to a medical institution in order to determine whether a body is abnormal, an additional expenditure occurs, and it takes an amount of time to confirm an examination result. Therefore, there was a drawback that the telemedicine was not efficiently performed.

SUMMARY OF THE INVENTION

In view of the above, the present invention provides an apparatus and method for self-examining whether a breast tissue is abnormal, capable of conveniently diagnosing whether an examinee's specific body part to be checked is abnormal without expensive medical equipments such as ultrasonic equipment, radiation equipment and magnetic field equipment, by embodying an examination checker that transmits a microwave to an examinee's body part to be examined such as a breast, receives a response microwave, and generates microwave information, and a self-examination device, installed in a mobile terminal such as a smart phone in a form of an application, that analyzes microwave information provided by the examination checker and determines whether an examinee's breast tissue is abnormal.

In accordance with a first aspect of the present invention, there is provided an apparatus for self-examining whether a breast tissue is abnormal. The apparatus includes an examination checker configured to transmit a microwave to one side of an examinee's breast, receive the microwave that has passed through the breast and calculate a value in the microwave reception of the received microwave; and a self-examination device configured to analyze the value in the microwave reception received from the examination checker and examines whether the breast is abnormal.

Further, the self-examination device may be configured to examine whether the breast is abnormal on the basis of a breast bilateral symmetry based determination method and an average evaluation value based determination method using the value in the microwave reception.

Further, the self-examination device may comprise an examination checker connection unit being connected to the examination checker and configured to receive the value in the microwave reception; an information analysis unit configured to analyze the value in the microwave reception to examine whether the breast is abnormal; and an information storage unit that stores information needed to make a calculation and a determination to evaluate whether the breast is abnormal on the basis of the value in the microwave reception.

Further, the information storage unit may store a value in a microwave reception for each of the left and right breasts at an examination time point of the breast and an evaluation value for each of the left and right breasts calculated from the value in the microwave reception.

Further, the information storage unit may store an average evaluation value calculated by averaging the evaluation values stored from the examination time point to an N-th examination time point or an initialization termination time point and a determination threshold value calculated by applying the average evaluation value to determine whether the breast is abnormal.

Further, the information analysis unit may be configured to receive a value in a microwave reception executed from the examination time point for the breast to the N-th examination time point or the initialization termination time, calculate a determination threshold value to determine whether the breast is abnormal using the value in the microwave reception, and determine an abnormality of the breast when the change in the evaluation value of the value in the microwave reception exceeds the determination threshold value.

Further, the information analysis unit may be configured to produce the determination threshold value by calculating an average evaluation value of the value in the microwave reception and adding a predetermined constant value to the average evaluation value.

Further, the examination checker may comprise a connection unit configured to connect with the self-examination device; a microwave transmission unit configured to transmit the microwave to one side of the examinee's breast; a microwave reception unit configured to receive the microwave that has passed through the breast at the other side of the breast; a microwave calculation unit configured to calculate a value in the microwave reception for the microwave that has passed through the breast; and a control unit configured to control the microwave to be transmitted to the examinee's breast, and transmit the value in the microwave reception calculated from the microwave that has been received by way of the breast, to the self-examination device through the connection unit.

Further, the examination checker may further comprise a matching material disposed between the microwave transmission unit and the microwave reception unit so as to stick to the breast.

Further, the self-examination device may be installed in a mobile terminal as an application.

Further, the mobile terminal may comprise a smart phone, a tablet PC or a PDA.

In accordance with a second aspect of the present invention, there is provided a method for self-examining whether a breast tissue is abnormal. The method includes, in an examination checker, transmitting a microwave to one side of an examinee's breast and receiving the microwave that has passed through the breast at the other side of the breast; in the examination checker, calculating a value in the microwave reception of the received microwave; in a self-examination device connected to the examination checker, receiving the value in the microwave reception; and in the self-examination device, analyzing the value in the microwave reception to examine whether the breast is abnormal.

Further, the analyzing the value in the microwave reception may be performed using a breast bilateral symmetry based determination method and an average evaluation value based determination method using the value in the microwave reception.

Further, the analyzing the value in the microwave reception may comprise calculating a determination threshold value to determine whether the breast is abnormal using a value in the microwave reception executed from an examination time point for the breast to an N-th examination time point or an initialization termination time point; examining whether the change in an evaluation value exceeds the determination threshold value; and determining that the breast is abnormal when exceeding the determination threshold value.

Further, the calculating a determination threshold value may comprise calculating an average evaluation value of the value in the microwave reception; and producing the determination threshold value by adding a predetermined constant value to the average evaluation value.

In accordance with the present invention, when self-examining whether a breast tissue is abnormal, there is an advantage capable of conveniently diagnosing whether an examinee's specific body part to be checked is abnormal without expensive medical equipments such as ultrasonic equipment, radiation equipment and magnetic field equipment, by embodying an examination checker that transmits a microwave to an examinee's body part to be examined such as a breast, receives a response microwave, and generates microwave information and a self-examination device, which is installed in a mobile terminal such as a smart phone in a form of an application, that analyzes microwave information provided by the examination checker and determines whether an examinee's breast tissue is abnormal.

BRIEF DESCRIPTION OF THE DRAWINGS

The above and other objects and features of the present invention will become apparent from the following description of the embodiments given in conjunction with the accompanying drawings, in which.

DETAILED DESCRIPTION OF THE EMBODIMENTS

Hereinafter, embodiments of the present invention will be described in detail with reference to the accompanying drawings.

In the following description of the present invention, if the detailed description of the already known structure and operation may confuse the subject matter of the present invention, the detailed description thereof will be omitted. The following terms are terminologies defined by considering functions in the embodiments of the present invention and may be changed operators intend for the invention and practice. Hence, the terms need to be defined throughout the description of the present invention.

Figure 2:
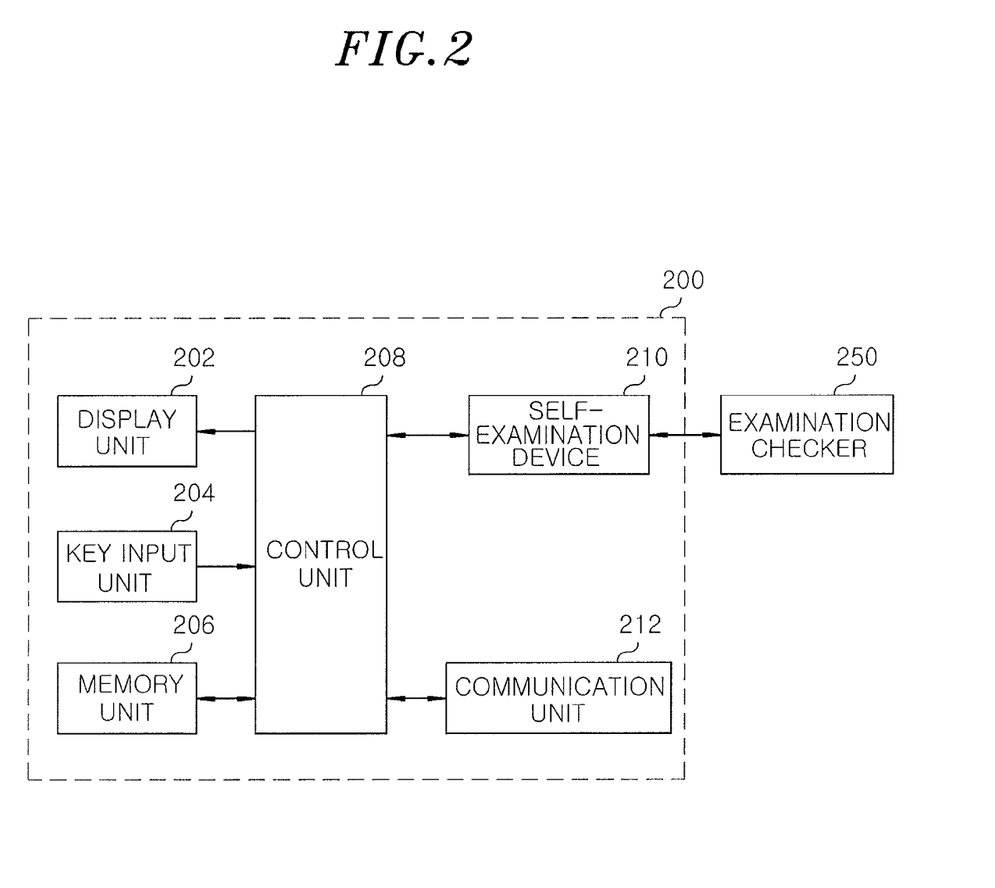
FIG. 2 is a detailed block diagram of a mobile terminal having an apparatus for self-examining whether a breast tissue is abnormal in accordance with an embodiment of the present invention.

FIG. 2 is a detailed block diagram of a mobile terminal having an apparatus for self-examining whether a breast tissue is abnormal in accordance with an embodiment of the present invention. Such a mobile terminal may include a terminal such as a smart phone, a tablet PC and a PDA (personal digital assistant).

Hereinafter, each component in the mobile terminal and operations of a self-examination device will be described in detail with reference to FIG. 2.

First, a key input unit 204 may be composed of a number of numeral keys and function keys to request a variety of operations of the mobile terminal 200. When a user presses a certain key, the key input unit 204 generates key data corresponding to the pressed key and outputs it to a control unit 208. Such a key input unit 204 has different character arrangements depending on manufacturers, and nations. Further, in case of a smart phone, a tablet PC, or the like, the key input unit 204 may be displayed on a display unit 202 in a touch screen form when necessary, that is, in a software form, instead of a physical keypad.

A communication unit 212 is connected to the Internet via a wired/wireless network and perform data communication. The display unit 202 displays different information of the mobile terminal 200 under the control of the control unit 208, and receives the key data generated by the key input unit 204 and different information signal of the control unit 208 for displaying them.

The control unit 208 controls overall operations of the mobile terminal 200 in accordance with an operational program stored in the memory unit 206. Such an operational program commonly refers to software programmed in advance when it is manufactured to connect the display unit 202 and the key input unit 204 with each other, manage data input/output, and operate internal applications of the terminal 200, as well as a basic operating system needed to operate the terminal 200.

The self-examination device 210 may be an application that enables the mobile terminal 200 to self-examine whether a breast tissue is abnormal. It may be previously programmed and installed in the mobile terminal 200 when the terminal 200 is manufactured, or downloaded and installed in the mobile terminal 200 via the communication unit 212 after the mobile terminal 200 has been manufactured.

The self-examination device 210 is provided with microwave information such as a microwave reception value having information on the breast tissue from an examination checker 250 which sticks to an examinee's breast or the like to transmit a microwave to a breast tissue and receive the microwave that has passed through the breast tissue. Further, the self-examination device 210 analyzes the microwave information, determines whether the examinee's breast tissue to be self-examined is abnormal and outputs its result.

A detailed block and operations of the self-examination device 210 and the examination checker 250 will be described in detail with reference to FIG. 3.

Figure 3:
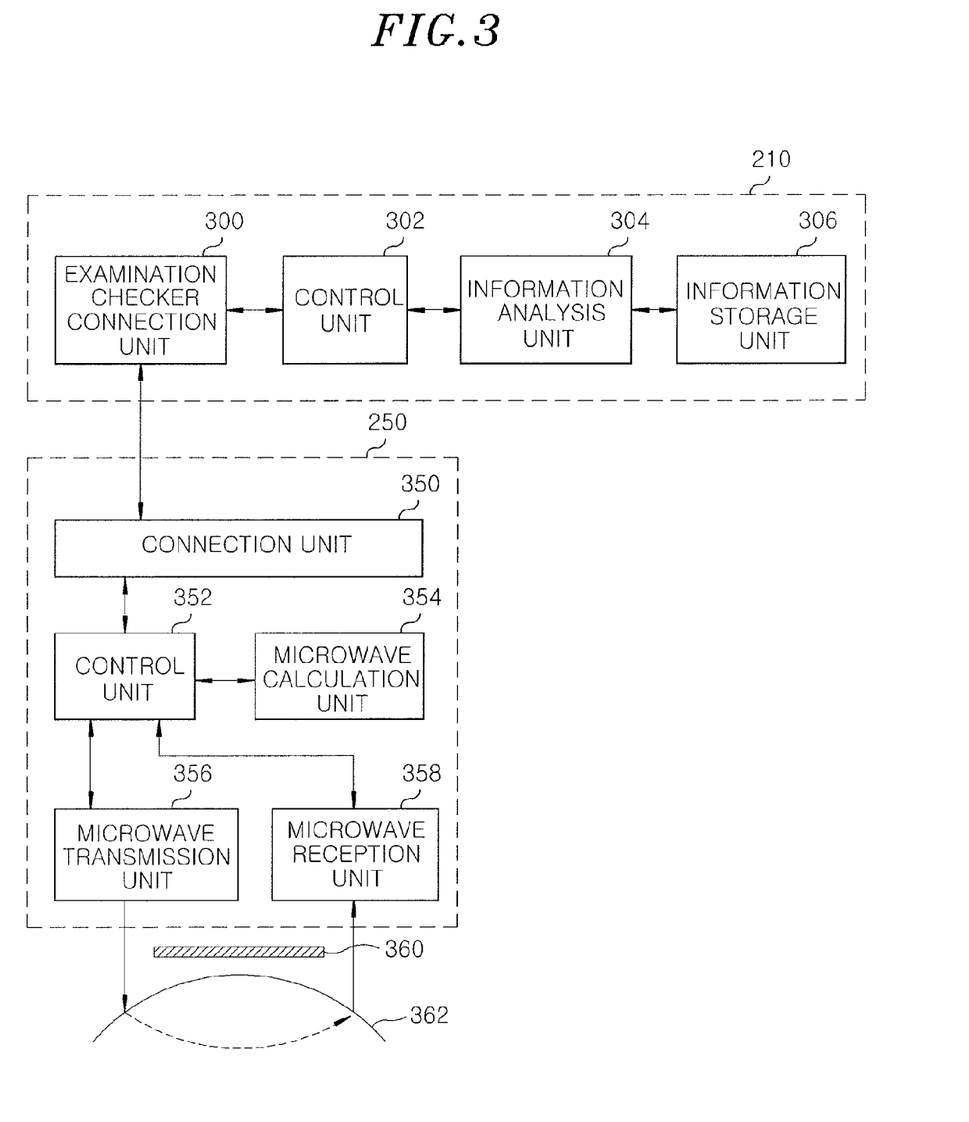
FIG. 3 is a detailed block diagram of an apparatus for self-examining whether a breast tissue is abnormal in accordance with an embodiment of the present invention.

FIG. 3 is a detailed block diagram of an apparatus for self-examining whether a breast tissue is abnormal, which includes the self-examination device 210 and the examination checker 250, in accordance with an embodiment of the present invention.

Hereinafter, the operations of each component of the self-examination device 210 and the examination checker 250 will be described in detail with reference to FIG. 3.

First, the self-examination device 210 includes an examination checker connection unit 300, a control unit 302, an information analysis unit 304, and an information storage unit 306.

The examination checker connection unit 300 is connected to the examination checker 250 and receives microwave examination information for a breast tissue. The control unit 302 generally controls operations of the self-examination device 210 in accordance with a control program stored in advance.

The information analysis unit 304 performs a final determination on whether the breast tissue is abnormal using a calculation for evaluating whether the breast tissue is abnormal, a determination method based on bilateral symmetry and a determination method based on average evaluation value based. The information storage unit 206 stores information needed to make a calculation and a determination for evaluating whether the breast tissue is abnormal.

Meanwhile, the examination checker 250 includes a connection unit 350, a control unit 352, a microwave calculation unit 354, a microwave transmission unit 356, and a microwave reception unit 358. Further, such an examination checker 250 sticks to an examinee's specific part of a body, for example, a breast, by a matching material 360, and performs an examination using a microwave.

The connection unit 350 is connected to external equipment such as the self-examination device 210 and performs a communication with the self-examination device 210. The control unit 352 controls overall operations of the examination checker. The microwave transmission unit 356 transmits a microwave for examination to the breast. The microwave reception unit 358 receives the microwave that has been transmitted from the microwave transmission unit 356 and has passed through the examinee's breast.

The microwave calculation unit 354 calculates a value in the microwave reception received through the microwave reception unit 358. The value in the microwave reception calculated is provided to the control unit 352, and the control unit 352 provides the value in the microwave reception value that has examined the examinee's breast to the self-examination device 210 through the connection unit 350.

Hereinafter, the method for self-examining whether a breast tissue is abnormal will be described in more detail. First, in a preparation procedure of self-examining whether a breast tissue is abnormal, an examinee who examines whether a breast is abnormal executes the self-examination device 210 that may be installed as an application in a mobile terminal 200 such as a smart phone and connects the examination checker 250 through a wired connection cable or via wireless connection.

Subsequently, the examinee 362 sticks the microwave transmission unit 356 of the examination checker 250 and the microwave reception unit 358 of the checker 250 to an examinee's breast 362. At this time, a matching material 360 may be placed on the breast 362 between the microwave transmission unit 356 and the microwave reception unit 358 in order that a microwave may be smoothly transmitted through the microwave transmission unit 356 of the examination checker 250, the examinee's breast 362, and the microwave reception unit 358 of the examination checker 250.

Next, at a procedure of self-examining whether a breast tissue is abnormal, an examinee whose breast is abnormal executes the self-examination device 210.

Thereafter, a control unit 302 of the self-examination device 210 is connected to the examination checker 250 through the examination checker connection unit 300 and then requests it to perform a microwave examination of the breast 362 to be examined.

Such a request is applied to a control unit 352 of the examination checker 250 through the connection unit 350 of the examination checker 250, and the control unit 352 enables the microwave transmission unit 356 to transmit a microwave to the breast 362, which is a part of a body to be examined, through the microwave transmission unit 356.

The microwave transmitted to the breast 362 is received by the microwave reception unit 358 by way of the breast 362, and the received microwave is transferred to the microwave calculation unit 354. Then, the microwave calculation unit 354 calculates a value in the microwave reception using the microwave that is received by way of the examinee's breast 362.

At this time, the value in the microwave reception calculated at the microwave calculation unit 354 has values that are characterized by whether the examinee's breast tissue is abnormal and changes such as scattering or reflection of the microwave in accordance with the abnormality or impedance of the breast tissue.

Such values in the microwave reception are transferred to the self-examination device 210 by the control unit 352 of the examination checker 250. The control unit 302 of the self-examination device 210 then receives the values in the values in the microwave reception through the examination checker connection unit 300 and provides the information analysis unit 304 with the values in the microwave reception.

Accordingly, the information analysis unit 304 manages the values in the microwave reception, performs a calculation to determine whether the breast tissue is abnormal, and determines whether the examinee's breast tissue is abnormal using a bilateral symmetry based determination method or an average evaluation value based determination method. During the determination, the information storage unit 306 stores information needed in the information analysis unit 304 and outputs or deletes the information in accordance with a predetermined control.

Figure 4:
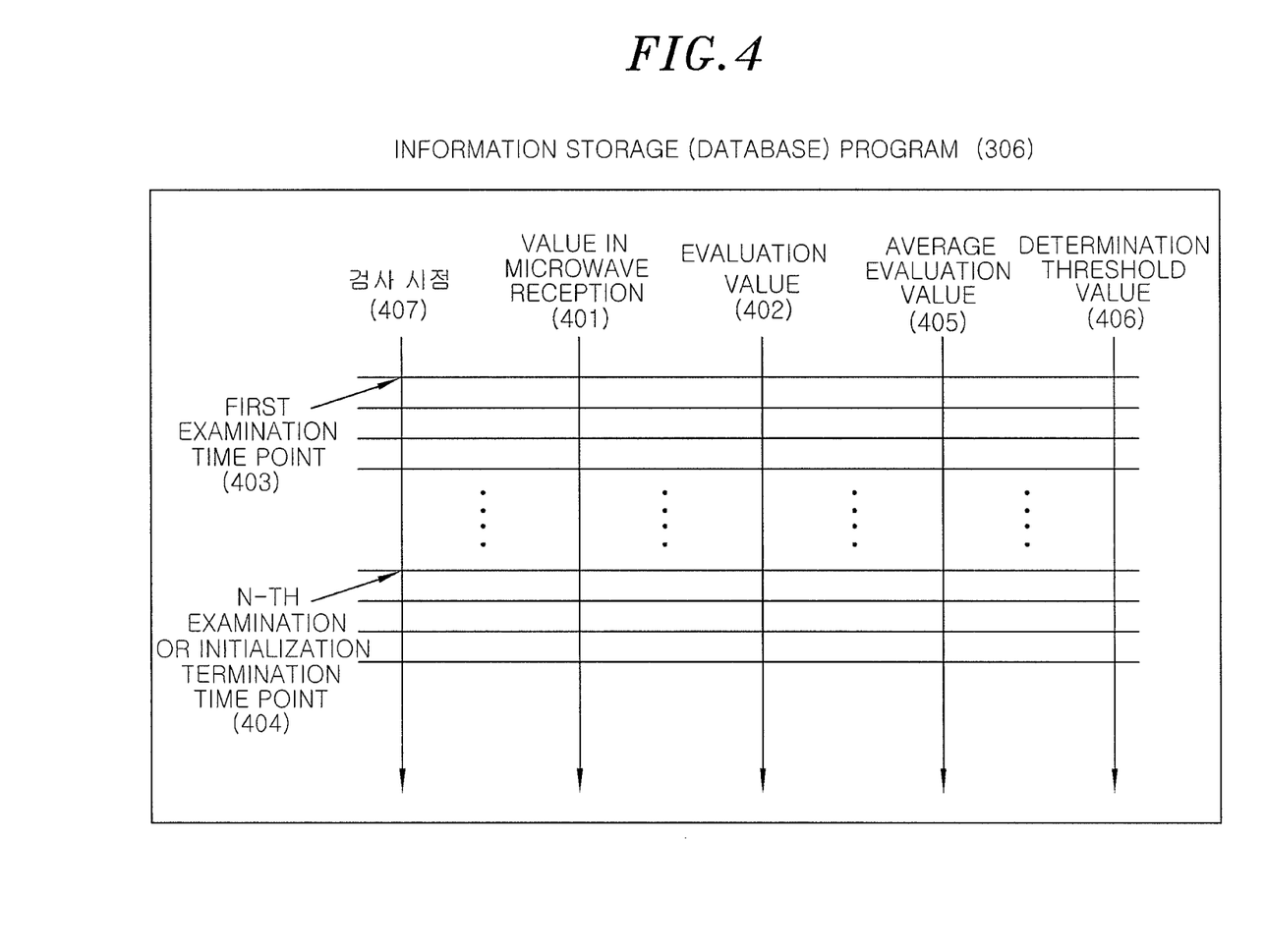
FIG. 4 is a data configuration diagram in an information storage unit in accordance with an embodiment of the present invention.

FIG. 4 illustrates a concept of information contents and information configuration stored and arranged in the information storage unit 306 in accordance with an embodiment of the present invention.

Referring to FIG. 4, the information storage unit 306 stores an examination time point 407, a value in a microwave reception 401 for each of the left and right breasts, and an average value 402 for each of the left and right breasts calculated from the value in the microwave reception 401.

Further, the information storage unit 306 stores an average evaluation value 405 calculated by averaging evaluation values stored in the information storage unit 306 from a first examination time point 403 to an arbitrary N-th examination or an initialization termination time point 404 and a determination threshold value 406 calculated by applying the average evaluation value 405 to determine whether the examinee's breast tissue is abnormal. In this regard, the evaluation value 402 used to determine whether the examinee's breast tissue is abnormal is a difference between a value in the microwave reception or a reference value, which is derived from a normal breast tissue, and a value in the microwave reception at an examination time point, and it can be calculated by a functional formula of a following Equation 1.

$$E = F(|S_n - S_0|) \qquad \text{Eq. 1}$$

In the Equation 1, E denotes the evaluation value 402, $S_n$ denotes the value in the microwave reception 401 at the examination time point, and $S_0$ denotes the microwave reception value or reference value of the normal breast tissue.

Figure 5:
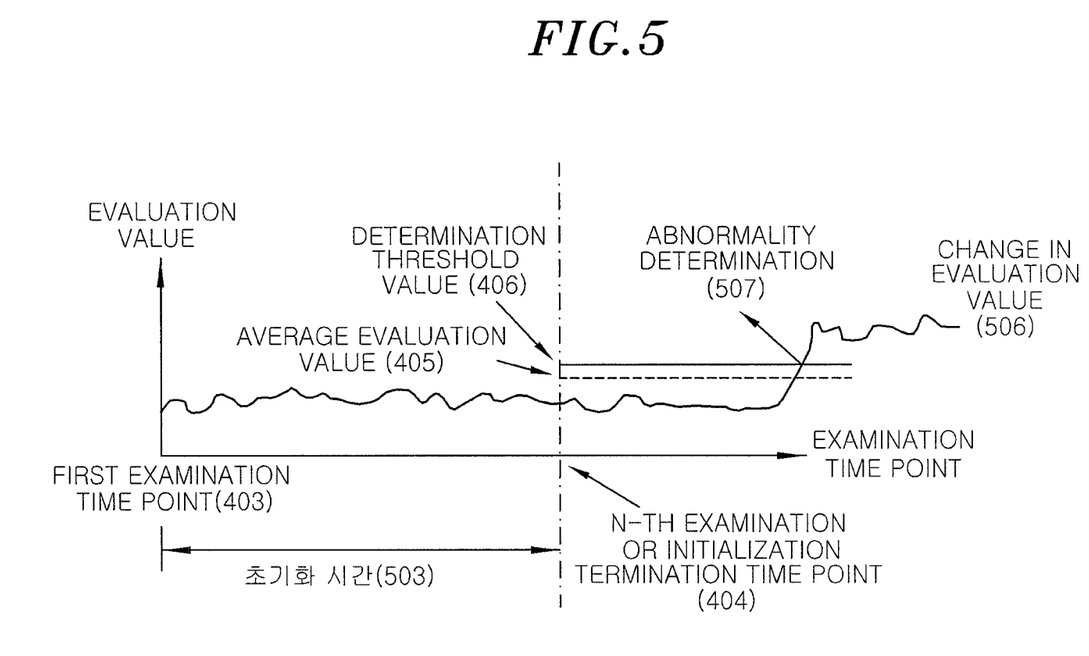
FIG. 5 is a conceptual diagram illustrating whether a breast tissue is abnormal in an information analysis unit in accordance with an embodiment of the present invention.

FIG. 5 illustrates a conceptual operation to determine whether a breast tissue is abnormal in an information analysis unit in accordance with an embodiment of the present invention.

Referring to FIG. 5, when self-examining whether a breast tissue is abnormal, the examination checker 250 performs an examination using a microwave for a breast 362 to be examined, and provides the self-examination device 210 with a value in the microwave reception received in the microwave reception unit 358.

Then, the information analysis unit of the self-examination device 210 receives the value in the microwave reception which has been repeatedly examined from a first examination time point 403 to an N-th examination or initialization termination time point 404, and accumulates an N×2 number of bilateral breast evaluation values when a predetermined initialization time 503 has elapsed. Subsequently, the information analysis unit 304 calculates an average evaluation value 405 of these evaluation values and calculates a determination threshold value 406 by adding a constant value used to enhance the determination accuracy to the average evaluation value 405. Thereafter, it is examined whether the evaluation value change 506 exceeds the determination threshold value 406 from an N-th examination or a (N+1)-th examination, and an abnormality determination 507 is made for the examinee's breast when exceeding the determination threshold value 406.

As described above, in accordance with the present invention, there is provided an apparatus and method for self-examining whether a breast tissue is abnormal, capable of conveniently diagnosing whether an examinee's specific body part to be checked is abnormal without expensive medical equipments such as ultrasonic equipment, radiation equipment and magnetic field equipment, by embodying an examination checker that transmits a microwave to an examinee's body part to be examined, such as a breast, receives a response microwave, and generates microwave information, and a self-examination device installed in a mobile terminal such as a smart phone in a form of an application that analyzes microwave information provided by the examination checker and determines whether an examinee's breast tissue is abnormal.

While the invention has been shown and described with respect to the embodiments, the present invention is not limited thereto. It will be understood by those skilled in the art that various changes and modifications may be made without departing from the scope of the invention as defined in the following claims.

What is claimed is:

1. An apparatus for self-examining whether a breast tissue is abnormal, the apparatus comprising:
    an examination checker configured to transmit a microwave to one side of an examinee's breast, receive the microwave that has passed through the breast and calculate a value in the microwave reception of the received microwave; and
    a self-examination device configured to analyze the value in the microwave reception received from the examination checker and examines whether the breast is abnormal,
    wherein the self-examination device comprises:
        an examination checker connection unit being connected to the examination checker and configured to receive the value in the microwave reception;
        an information analysis unit configured to analyze the value in the microwave reception to examine whether breast is abnormal; and
        an information storage unit that stores information including a reference value needed to make a calculation and a determination to evaluate whether the breast is abnormal on the basis of the value in the microwave reception
        wherein the information storage unit stores the value in a microwave reception for the examinee's breast at an examination time point of the breast and an evaluation value for the examinee's breast is calculated from the value in the microwave reception, the evaluation value being the difference between the value in the microwave reception and the reference value, which is derived from normal breast tissue, and a value in the microwave reception at the examination time point.

2. The apparatus of claim 1, wherein the self-examination device is configured to examine whether the breast is abnormal on the basis of a breast bilateral symmetry based determination method and an average evaluation value based determination method using the value in the microwave reception.

3. The apparatus of claim 1, wherein the information storage unit stores a value in a microwave reception for each of the left and right breasts at the examination time point of the breast and an evaluation value for each of the left and right breasts calculated from the value in the microwave reception.

4. The apparatus of claim 3, wherein the information storage unit stores an average evaluation value calculated by averaging the evaluation values stored from the examination time point to an N-th examination time point or an initialization termination time point and a determination threshold value calculated by applying the average evaluation value to determine whether the breast is abnormal.

5. The apparatus of claim 1, wherein the information analysis unit is configured to receive a value in a microwave reception executed from the examination time point for the breast to the N-th examination time point or the initialization termination time, calculates a determination threshold value to determine whether the breast is abnormal using the value in the microwave reception, and determines an abnormality of the breast when the change in the evaluation value of the value in the microwave reception exceeds the determination threshold value.

6. The apparatus of claim 5, wherein the information analysis unit is configured to produce the determination threshold value by calculating an average evaluation value of the value in the microwave reception and adding a predetermined constant value to the average evaluation value.

7. The apparatus of claim 1, wherein the examination checker comprises:
   a connection unit configured to connect with the self-examination device;
   a microwave transmission unit configured to transmit the microwave to one side of the examinee's breast;
   a microwave reception unit configured to receive the microwave that has passed through the breast at the other side of the breast;
   a microwave calculation unit configured to calculate a value in the microwave reception for the microwave that has passed through the breast; and
   a control unit configured to control the microwave to be transmitted to the examinee's breast, and transmit the value in the microwave reception calculated from the microwave that has been received by way of the breast, to the self-examination device through the connection unit.

8. The apparatus of claim 7, wherein the examination checker further comprises:
   a matching material disposed between the microwave transmission unit and the microwave reception unit so as to stick to the breast.

9. The apparatus of claim 1, wherein the self-examination device is installed in a mobile terminal as an application.

10. The apparatus of claim 9, wherein the mobile terminal comprises a smart phone, a tablet PC or a PDA.

11. The apparatus of claim 10, wherein the self-examination device communicates with the examiner checker by wireless communication.

12. A method for self-examining whether a breast tissue is abnormal, the method comprising:
   in an examination checker, transmitting a microwave to both sides of an examinee's breast by N+1 times from a first examination time point to an N+1th examination time point, and receiving the microwave that has passed through the breast at the other side of the breast, where N is a positive integer;
   in the examination checker, calculating 2N+2 values in the microwave reception of the microwave received N+1 times;
   in a self-examination device connected to the examination checker, receiving the 2N+2 values in the microwave reception; and
   in the self-examination device, analyzing the 2N+2 values in the microwave reception to examine whether the breast tissue is abnormal,
   wherein said analyzing the 2N+2 values in the microwave reception comprises:
   calculating an average evaluation value based on 2N values in the microwave reception obtained from the both sides of the breast by transmitting the microwave N times from the first examination time point to an N-th examination time point and an evaluation value based on a value in the microwave reception obtained from one side of the breast to be examined by transmitting the microwave at the N+1-th examination time point;
   producing a determination threshold value by adding a predetermined constant value to the average evaluation value;
   examining whether the evaluation value exceeds the determination threshold value; and
   determining that the one side of the breast is abnormal when the evaluation value exceeds the determination threshold value.

13. The method of claim 12, wherein said analyzing the value in the microwave reception is performed using a breast bilateral symmetry based determination method and an average evaluation value based determination method using the value in the microwave reception.

* * * * *